US005479471A

United States Patent [19]
Buckland

[11] Patent Number: 5,479,471
[45] Date of Patent: Dec. 26, 1995

[54] FOOT HOLDING AND POSING APPARATUS FOR X-RAY EXAMINATION

[76] Inventor: Peter E. Buckland, 17835 NW. 63rd Ct., Miami, Fla. 33015

[21] Appl. No.: 232,816

[22] Filed: Apr. 22, 1994

[51] Int. Cl.⁶ ............................................. A61B 6/04
[52] U.S. Cl. .................... 378/208; 378/204; 128/882; 128/845
[58] Field of Search ................... 378/208, 204, 378/209; 128/845, 846, 869, 878, 879, 882; 602/20, 21, 23, 27, 60, 61, 62, 65, 66

[56] References Cited

U.S. PATENT DOCUMENTS

| | | | |
|---|---|---|---|
| 4,232,681 | 11/1980 | Tulaszewski | 378/208 X |
| 4,320,749 | 3/1982 | Highley | 128/83 |
| 4,323,080 | 4/1982 | Melhart | 378/208 X |
| 4,407,277 | 10/1983 | Ellison | 378/208 X |
| 4,443,005 | 4/1984 | Sugarman et al. | 269/328 |
| 4,492,225 | 1/1985 | Picolet et al. | |
| 4,573,482 | 3/1986 | Williams, Jr. | 128/845 |
| 4,827,496 | 5/1989 | Cheney | 378/180 |
| 5,020,523 | 6/1991 | Bodine | 128/882 X |
| 5,094,232 | 3/1992 | Harris et al. | 602/27 X |
| 5,242,379 | 9/1993 | Harris et al. | 602/27 |
| 5,267,949 | 12/1993 | De La Torre et al. | 128/882 X |

Primary Examiner—David P. Porta
Attorney, Agent, or Firm—Frank L. Kubler

[57] ABSTRACT

An apparatus for positioning a human foot for X-ray examination on an apparatus support surface, the human foot having a foot bottom surface, a foot rear surface and two foot side surfaces, includes structure for retaining the foot including a foot retaining bottom portion extending over the foot bottom surface, a foot retaining rear portion extending over the foot rear surface and a foot retaining side portion extending over at least one of the foot side surfaces, and structure for propping and orienting the foot including a substantially horizontal base member for resting on the apparatus support surface and for supporting the foot and the structure for retaining, the base member having laterally distributed contact activated fasteners for engaging the foot retaining rear portion at any of several laterally distributed points along the base member for securing left and right feet, and including a substantially vertical upright member for positioning the foot and the structure for retaining, the upright member being secured to and braced against rotation by the base member and having an upright foot positioning member surface with laterally distributed contact activated fasteners for engaging the foot retaining bottom portion at any of several laterally distributed points to retain the foot in a selected angular orientation relative to the base member.

5 Claims, 3 Drawing Sheets

FOOT HOLDING AND POSING APPARATUS FOR X-RAY EXAMINATION

BACKGROUND OF THE INVENTION

1. Field of the Invention

The present invention relates generally to the field of body securing devices for X-ray examinations. More specifically, it relates to a foot orienting and securing apparatus which is low in cost, disposable and specifically designed for use in sterile environments where patient cooperation is not available, including a foot retaining structure and a foot prop structure. The retaining structure is preferably in the form of an open top boot with foot retaining strap means. The prop structure preferably has a horizontal base plate for supporting the rear of the boot heel and a vertical positioning plate extending from the base plate for abutting and anchoring the bottom of the foot in a selected rotational position. The foot retaining structure is removably and fixedly joinable to the two plates of the positioning structure by contact-activated fastening means. These fastening means may be hook and loop fastener strips, an adhesive, or interlocking male and female engaging members such as pegs and peg receiving holes. These fastening means extend laterally across the plates so that the base plate receives and engages the rear heel of the foot retaining structure at any lateral location along the base plate, and such that the vertical plate receives and engages the bottom of the foot retaining structure with the foot retaining structure rotated to any one of an infinite variety of rotational positions. An X-ray film cartridge or cassette prop structure is optionally provided in the form of a plate member having at least one set of two tab portions extending perpendicularly from the plate member to resiliently and retainingly receive between them an edge of an X-ray cassette.

2. Description of the Prior Art

There have recently been several devices for holding a leg and foot of a patient in desired positions for X-ray examination. These devices have generally been expensive and complex, requiring of patient assistance unavailable during surgery and most often not suited to rotationally orienting the foot.

One prior device is that of Cheney, U.S. Pat. No. 4,827,496, issued on May 2, 1989. Cheney teaches a leg and ankle holder including a base portion with a channel-shaped recess in its upper surface for receiving a heel and lower leg. A film cassette holding compartment having cassette positioning means is provided within the base portion. The bottom of the foot rests against a first plate extending upward from one end of the base portion. The first plate is pivotally mounted to a second plate immediately behind the first plate and secured thereto with a sliding clamp. The second plate has an arched top edge and the sliding clamp rides along the arch. Moving the sliding clamp pivots the first plate and foot about the heel of the foot, and then the clamp is tightened to hold the foot in the desired position. A second pivot point permits pivoting the foot at the ankle to extend or raise the end of the foot. A problem with Cheney is that it is complex and expensive to manufacture, and thus may necessarily be used for more than one patient. The guarantee of sterility, which is probably more important than ever today, would be lost in this event. Another problem with Cheney is that it could be awkward to use. Rather than simply setting the foot in the desired position, one must hold the foot in place while operating a dial to loosen and tighten the sliding clamp.

A device similar to that of Cheney is a foot support and positioner known as a "space boot" for preventing foot drop, such as that made by NUMEDICO™ Rehab Equipment and Supplies. A contoured foam "boot" is anchored to a support base with a vertical plate portion. A threaded pivoting bolt extends from the heel of the boot through a slot in the vertical plate and a knurled nut placed on the pivoting bolt secures the boot at that point. A threaded positioning bolt extends from the central sole of the boot through other converging slots in the vertical plate so that the boot can be fastened with a second knurled nut into any of several rotated positions against the vertical plate. The problems of Cheney are again presented.

Highley, U.S. Pat. No. 4,320,749, issued on Mar. 23, 1982, discloses an apparatus for facilitating X-ray examinations in which it is determined whether an anterior talo fibular ligament has been ruptured. The lower leg is strapped to the upright portion of an L-shaped support structure, and the foot is strapped to a longitudinally sliding carriage on the laterally extending base portion of the structure. The heel of the foot is engaged by a wedge member on the carriage and pressure is applied by a piston and cylinder combination within the base portion to move the carriage away from the upright portion. While this carriage movement may be suited to the narrow purpose of examining the anterior talo fibular ligament, Highley does not permit rotation of the foot for examination at various angles. Another problem with Highley is its complexity and substantial manufacturing cost. Like Cheney, Highley would likely have to be reused for a series of patients to be cost effective, so that sterility is not assured.

Sugarman, et al., U.S. Pat. No. 4,443,005, issued on Apr. 17, 1984, reveals a device for supporting a patient's foot during surgery. Sugarman includes a positioning shaft having two co-acting first and second post members slidably mounted on the shaft. Means are provided for locking the post members in a desired position. A foot engaging plate protrudes from the second post member for forming into a cast constructed around a foot and ankle. A problem with Sugarman is that one must form a cast around a foot merely to anchor it for X-ray examination. Another problem with Sugarman is that the complex structure of shafts and posts, and tightening screws and knobs, would be expensive to manufacture.

It is thus an object of the present invention to provide a foot holding and positioning apparatus for X-ray examination which is simple and inexpensive to manufacture to be disposable, so that either the foot holding portion or the entire apparatus may be provided new and truly sterile for each patient.

It is another object of the present invention to provide such an apparatus which accommodates a full range of rotational foot positions from which X-ray examination can be made.

It is another object of the present invention to provide such an apparatus which will reduce operating time, exposure to radiation, and physician frustration by minimizing the frequency of repeat X-ray examination.

It is still another object of the present invention to provide such an apparatus which is easy for operating room staff to understand and to use and which is ambidextrous.

It is still another object of the present invention to provide such an apparatus with an optional, inexpensive and simple X-ray cassette positioning structure.

It is finally an object of the present invention to provide such an apparatus which is compact, light weight and readily portable.

SUMMARY OF THE INVENTION

The present invention accomplishes the above-stated objectives, as well as others, as may be determined by a fair reading and interpretation of the entire specification.

An apparatus is provided for positioning a human foot for X-ray examination on an apparatus support surface, the human foot having a foot bottom surface, a foot rear surface and two foot side surfaces, including structure for retaining the foot including a foot retaining bottom portion extending over the foot bottom surface, a foot retaining rear portion extending over the foot rear surface and a foot retaining side portion extending over at least one of the foot side surfaces, and structure for propping and orienting the foot including a substantially horizontal base member for resting on the apparatus support surface and for supporting the foot and the structure for retaining, the base member having laterally distributed contact activated fasteners for engaging the foot retaining rear portion at any of several laterally distributed points along the base member for securing left and right feet, and including a substantially vertical upright member for positioning the foot and the structure for retaining, the upright member being secured to and braced against rotation by the base member and having an upright foot positioning member surface with laterally distributed contact activated fasteners for engaging the foot retaining bottom portion at any of several laterally distributed points to retain the foot in a selected angular orientation relative to the base member.

The structure for retaining preferably includes an open top boot having a boot bottom wall, two opposing boot side walls and a boot rear wall, where the foot retaining bottom portion includes the boot bottom wall, the side portion includes one of the two opposing boot side walls, and the rear portion includes the boot rear wall and extends between the boot side walls. The contact-activated fasteners each preferably include a laterally elongate hook and loop fastening patch. The open top boot preferably includes a foot retaining strap. The base member preferably has an upper surface, and additionally includes left and right foot positioning markings on the upper surface of the base member.

BRIEF DESCRIPTION OF THE DRAWINGS

Various other objects, advantages, and features of the invention will become apparent to those skilled in the art from the following discussion taken in conjunction with the following drawings, in which.

DETAILED DESCRIPTION OF THE PREFERRED EMBODIMENTS

Figure 1:
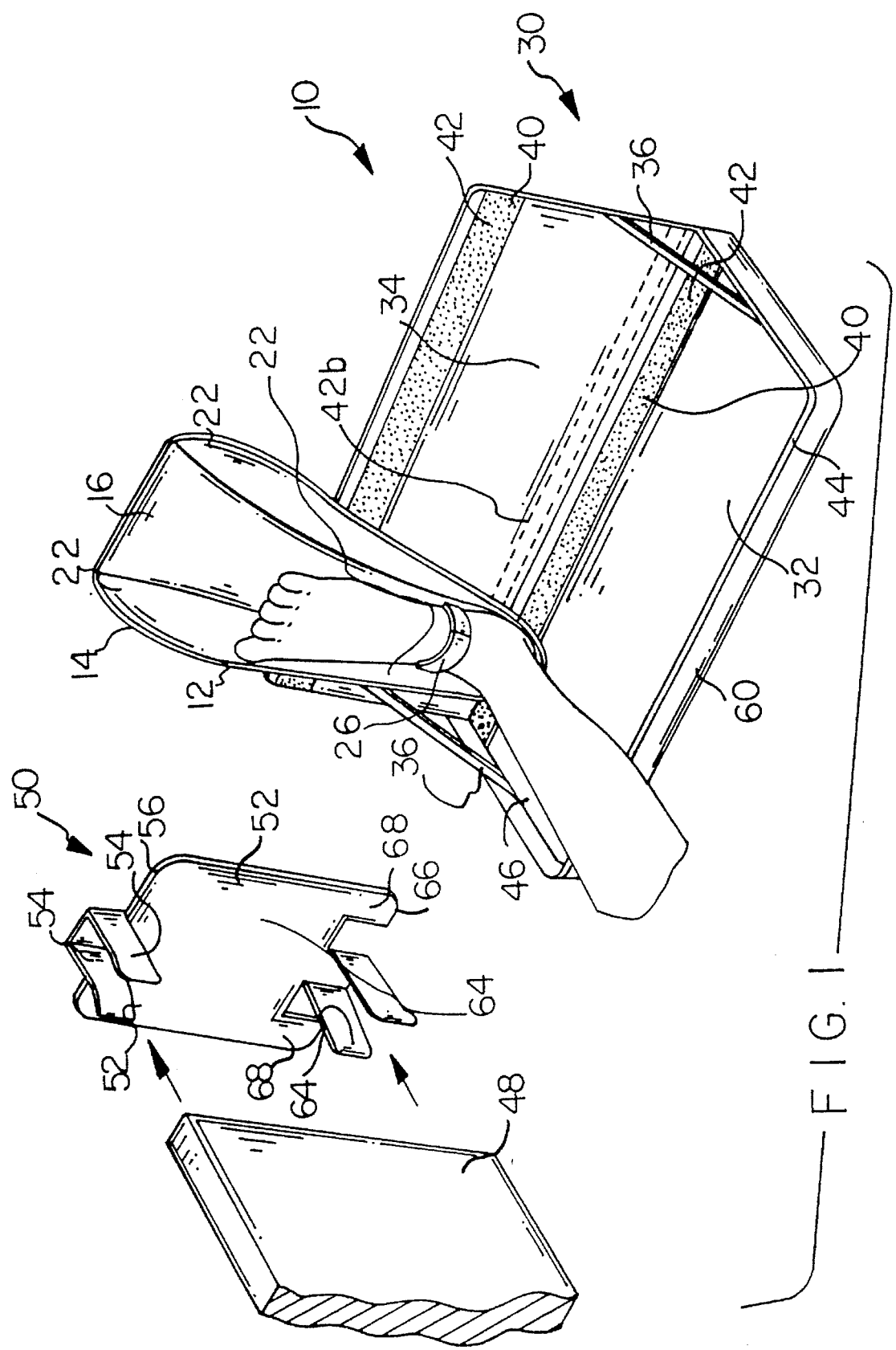
FIG. 1 is a perspective view of the inventive apparatus shown positioning a patient's foot for lateral X-ray examination, and a cassette is shown being moved toward engagement by the resilient tab portions of an inventive cassette retaining structure.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

Preferred Embodiment

Figure 2:
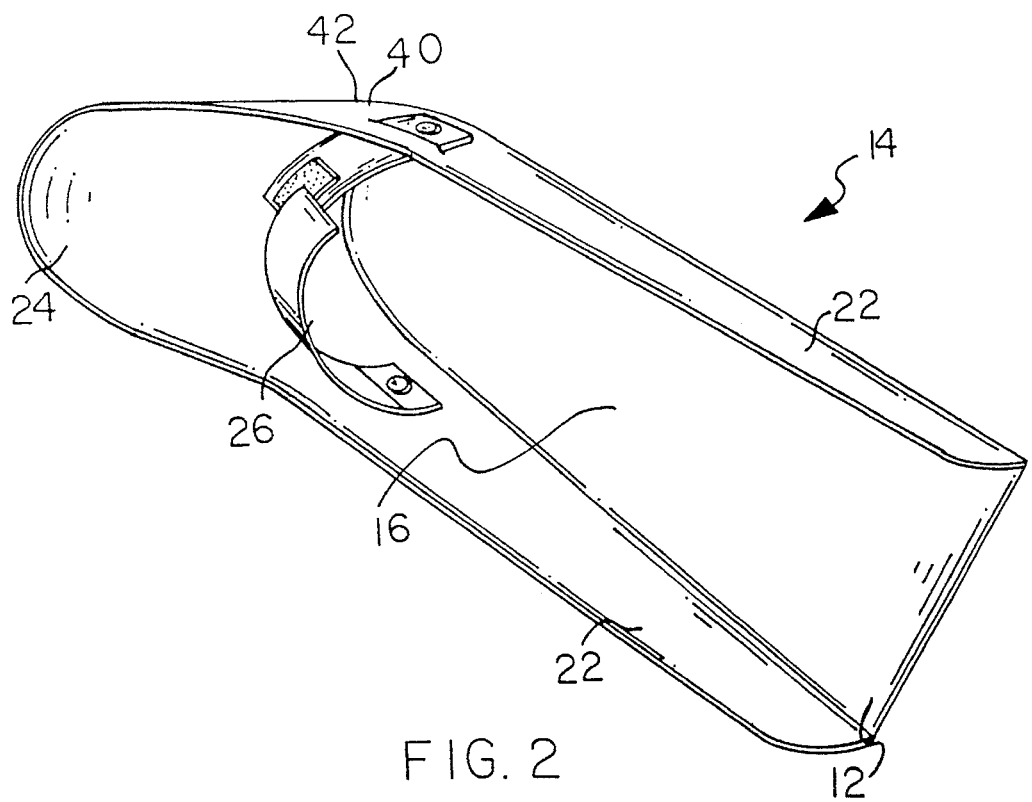
FIG. 2 is a perspective top view of the foot retaining boot.

Referring to FIG. 1, a foot holding and posing apparatus 10 is disclosed for holding either foot of a patient under general anesthesia in any of a wide variety of desired rotational positions for X-ray examination. Apparatus 10 includes an ambidextrous foot retaining structure 12 in the form of a disposable open top boot 14, preferably made of cardboard or an inexpensive plastic. See FIGS. 2 and 3. Boot 14 has a sole or bottom portion 16 against which the bottom of the foot rests. Side and rear boot walls 22 and 24, respectively, extend from bottom portion 16 to surround the sides and heel of the foot and thereby retain the foot within boot 14. Strap members 26 extend from the inner surfaces of side boot walls 22 to secure the boot 14 on the foot. Strap members 26 are preferably formed of flexible plastic and are removably secured together with either hook and loop fasteners 28 or an adhesive. Alternatively, a radiolucent buckle or a tied knot may join and tighten strap members 26 around a foot.

Figure 4:
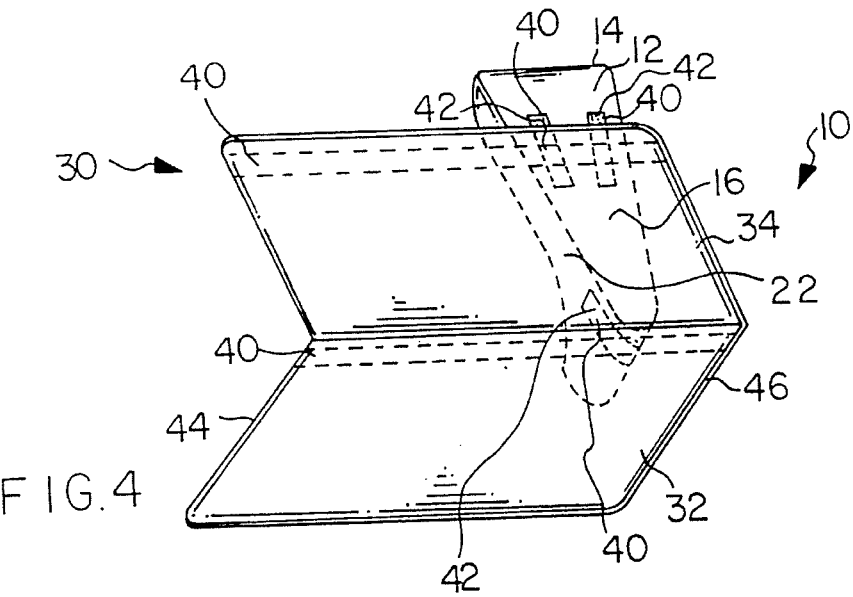
FIG. 4 is perspective back view of the prop structure and boot, with hidden edges shown in broken lines, to illustrate the mating fastening strips.

Apparatus 10 also includes a prop structure 30 for retaining and posing the boot 14 and foot in an infinite variety of rotational positions. See FIGS. 1 and 4. Prop structure 30 preferably includes a horizontal base plate 32 for abutting the rear boot wall 24 to support boot 14 and the foot. A vertical positioning plate 34 is joined to and extends upward from base plate 32 for orienting and retaining the boot 14 and foot in a selected rotational position about the heel and relative to base plate 32. Boot rear wall 24 is placed against base plate 32. The boot 14 and the foot are simply turned about the axis of the patient's leg to the desired rotational position. Then bottom wall 24 is placed against positioning plate 34 while in this position. Contact-activated fastening means 40 on boot 14, base plate 32 and positioning plate 34 grip and secure boot 14 against further rotational movement.

Support structure 30 as a whole props up the boot 14 and foot. Base plate 32 and positioning plate 34 must be sufficiently rigid and must be sufficiently secured together to prevent the weight of the foot (in its natural tendency to fall laterally) from collapsing by twisting or bowing of plate 34. Two load-bearing members 36, one at each end of prop structure 30, preferably extend between plates 32 and 34 to maintain a right angle of foot to leg.

Fastening means 40 are preferably hook and loop fastener strips 42 such as VELCRO™, and are provided on rear boot wall 24 and laterally across the upper surface of base plate 32. Other hook and loop fastener strips 42 are provided on the outer surface of boot bottom portion 16. See FIG. 4. A sufficient expanse or length of strip 42 is provided on plates 32 and 34 to permit full engagement of boot 14 at any lateral location or rotational position within prop structure 30.

Figure 5:
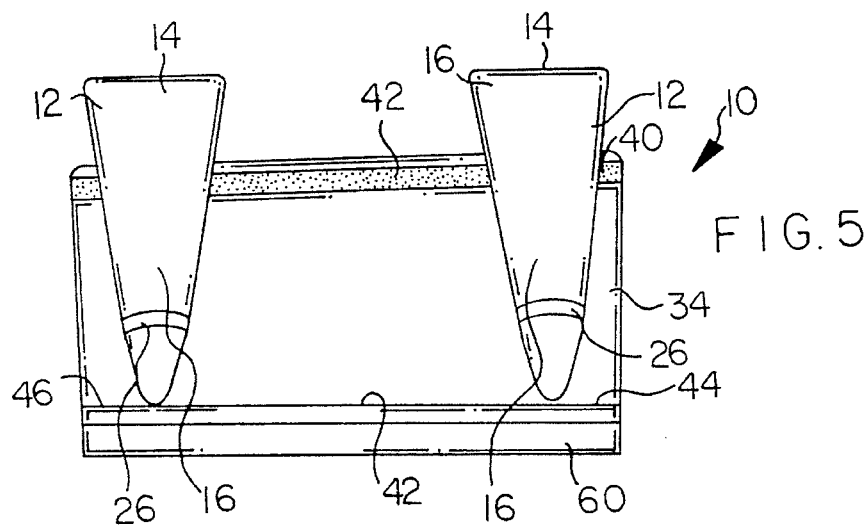
FIG. 5 is a front view of the prop structure showing the proper placing of a foot in a boot for left and for right feet. It is noted that both feet would not be on the base plate at the same time.

The anatomy of the human leg permits the left foot to rotate primarily to the left and the right foot to rotate primarily to the right. Therefore, the left foot is placed at the right end 44 of base plate 32 to maintain a vertical foot position and to allow X-ray cassette 40 to be placed in close proximity and proper position for any and all views (except oblique ankle) of foot, heel, ankle, and toes, before fastening means 40 engagement. The left foot tends to fall or exert a force rotationally to the left, and the rightward positioning of the left foot on base plate 32 leaves much of base plate 32 extending to the left of the left foot. See FIG. 5. This relationship permits base plate 32 to act as a stop lever abutting the operating table or other working surface to prevent rotation of prop structure 30 to the left. By the same token, the right foot is placed at the left end 46 of base plate 32 so that the foot can be placed and maintained in a vertical position for close proximity to the X-ray cassette 48. In each case, left and right obliques of an ankle require the rear boot wall 24 to be repositioned nearer the middle of base plate 32 with the toe end of boot 14 kept near its previous position. Also, once again, base plate 32 extends to the right of the right foot, which is the natural direction the foot tends to rotationally fall, to brace prop structure 30 against rotation to the right.

Contact-activated fastening means 40 may alternatively be an adhesive or may be interlocking male and female engaging members such as pegs and peg holes, or may be interlocking irregular or undulating surfaces.

Figure 6:
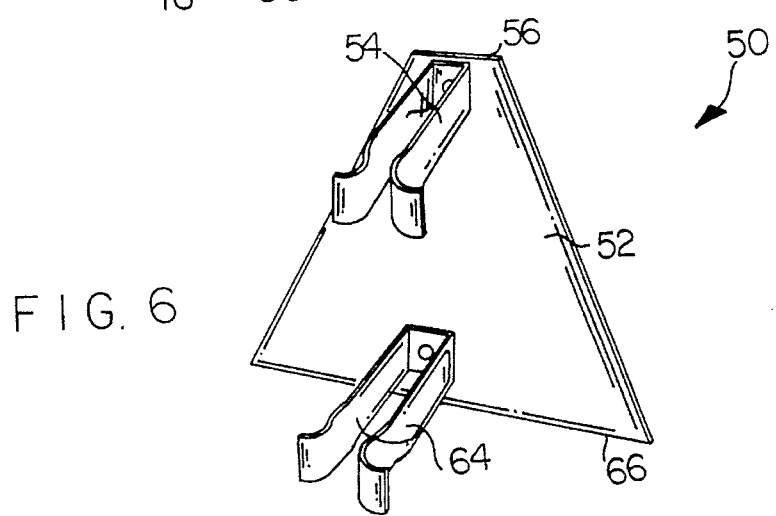
FIG. 6 is a perspective view of an alternative cassette retaining member design not having and not requiring the leg portions shown in FIG. 1.

An X-ray film cartridge or cassette 48 retaining structure 50 is preferably provided. Structure 50 takes the form of a rectangular plate member 52 having two ear or tab portions 54 cut and bent substantially perpendicularly outward from plate member end 56 in the same direction. See FIG. 1. Tab portions 54 are spaced apart from each other a sufficient distance to snugly receive an edge of an X-ray cassette 48. Tab portions 54 are resiliently biased toward each other to removably retain cassette 48 between them with a friction grip. A second pair of tab portions 64 are preferably cut from the opposing plate end 66, leaving portions of end 66 to serve as legs 68. Tab portions 64 are bent to engage a cassette 48 in the same manner described for tab portions 54. A foam pad is optionally adhered to inward surfaces of tab portions 54 and 64 to allow for variations in cassette 48 thicknesses while maintaining snugness of tab portion engagement. The free ends of tab portions 54 and tab portions 64 are preferably flared apart from each other to facilitate insertion of an edge of cassette 48 between them. Plate 52 and cassette 48 are substantially perpendicular to each other. As a result, they form in combination a T-shaped base which permits them to stand vertically, so that cassette 48 is oriented to receive an X-ray image. FIG. 6 shows an alternative retaining structure 50 where the tab portions 54 and 64 are sides of U-shaped channel sections attached to plate member 52. A bumper plate 60 is preferably placed underneath base plate 32 to elevate the foot relative to cassette 48 and assure a complete X-ray image. The corners of the various parts of apparatus 10 are preferably rounded for safety and to prevent puncturing of sterile cassette 48 bags or drapes. All parts of apparatus 10 are preferably radiolucent, and most parts are necessarily radiolucent.

Figure 3:
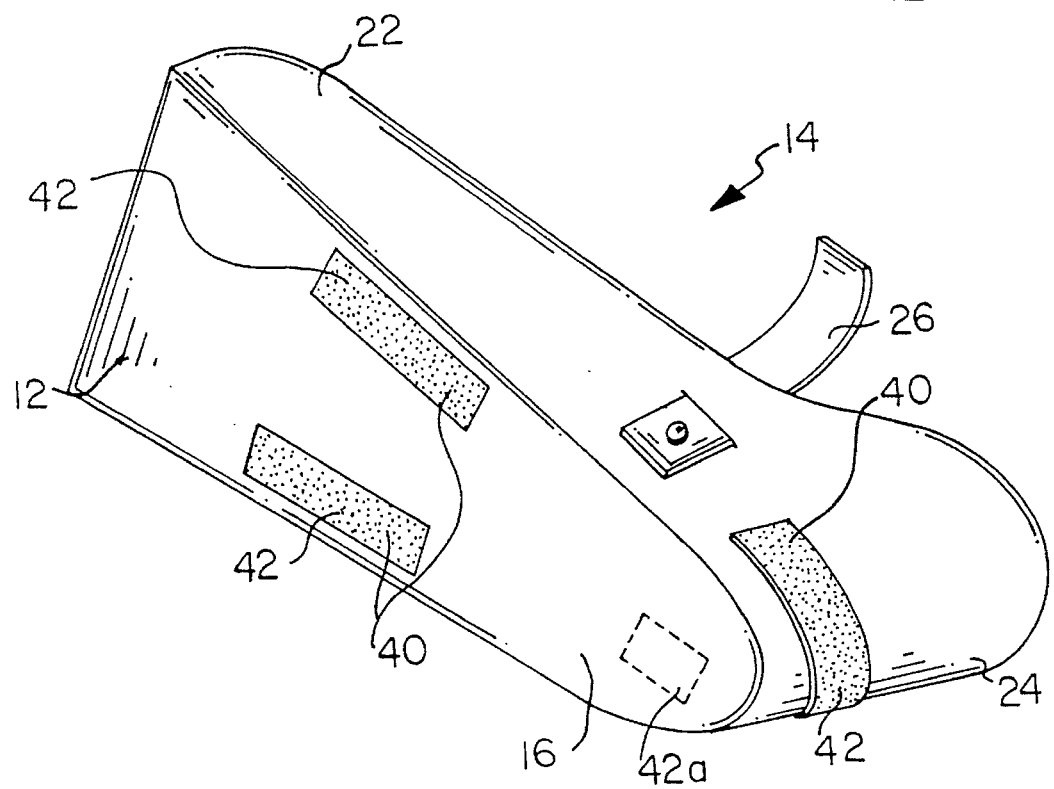
FIG. 3 is a perspective bottom view of the foot retaining boot.

An alternative design includes a hook and loop fastening means 42a on bottom portion 16 of boot 14, as shown in broken lines in FIG. 3, in place of fastening means 42 on rear boot wall 24. Fastening means 42a is engaged by a correspondingly located fastening means strip 40b on positioning plate 34 shown in broken lines in FIG. 1. Base plate 32 may be omitted.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim as my invention:

1. An apparatus for positioning a human foot for X-ray examination on an apparatus support surface, said human foot having a foot bottom surface, a foot rear surface and two foot side surfaces, comprising:

means for retaining said foot comprising a foot retaining bottom portion extending over said foot bottom surface, a foot retaining rear portion extending over said foot rear surface and a foot retaining side portion extending over at least one said foot side surface, means for propping and orienting said foot comprising a substantially horizontal base member for resting on said apparatus support surface and for supporting said foot and said means for retaining, said base member having laterally distributed contact activated fastening means for engaging said foot retaining rear portion at any of a plurality of laterally distributed points along said base member for securing left and right feet, and comprising a substantially vertical upright member for positioning said foot and said means for retaining, said upright member being secured to and braced against rotation by said base member and having an upright foot positioning member surface with laterally distributed contact activated fastening means for engaging said foot retaining bottom portion at any of a plurality of laterally distributed points to retain said foot in a selected angular orientation relative to said base member.

2. The apparatus of claim 1, wherein said means for retaining comprises an open top boot having a boot bottom wall, two opposing boot side walls and a boot rear wall, wherein said foot retaining bottom portion includes said boot bottom wall, said side portion includes one of said two opposing boot side walls, and said rear portion includes said boot rear wall and extends between said boot side walls.

3. The apparatus of claim 1, wherein said contact-activated fastening means each comprise a laterally elongate hook and loop fastening patch.

4. The apparatus of claim 2, wherein said open top boot comprises foot retaining strap means.

5. The apparatus of claim 1, wherein said base member has an upper surface, and additionally comprising left and right foot positioning markings on said upper surface of said base member.

* * * * *